(12) United States Patent
Heywood et al.

(10) Patent No.: US 10,472,426 B2
(45) Date of Patent: Nov. 12, 2019

(54) DISULFIDE STABILIZED DVD-IG MOLECULES

(75) Inventors: Sam Philip Heywood, Berkshire (GB); David Paul Humphreys, Berkshire (GB)

(73) Assignee: UCB BIOPHARMA SPRL, Brussels (BE)

( * ) Notice: Subject to any disclaimer, the term of this patent is extended or adjusted under 35 U.S.C. 154(b) by 463 days.

(21) Appl. No.: 13/637,211

(22) PCT Filed: Mar. 25, 2011

(86) PCT No.: PCT/GB2011/050613
§ 371 (c)(1),
(2), (4) Date: Dec. 10, 2012

(87) PCT Pub. No.: WO2011/117653
PCT Pub. Date: Sep. 29, 2011

(65) Prior Publication Data
US 2013/0302336 A1 Nov. 14, 2013
US 2016/0244532 A2 Aug. 25, 2016

(30) Foreign Application Priority Data
Mar. 25, 2010 (GB) .................................. 1005061.5
Mar. 25, 2010 (GB) .................................. 1005062.3

(51) Int. Cl.
| C07K 16/46 | (2006.01) |
| C08G 59/14 | (2006.01) |
| C08G 59/06 | (2006.01) |
| C08L 63/00 | (2006.01) |
| C09D 163/00 | (2006.01) |
| C09J 163/00 | (2006.01) |
| C08K 5/01 | (2006.01) |

(52) U.S. Cl.
CPC .......... *C07K 16/468* (2013.01); *C08G 59/066* (2013.01); *C08G 59/145* (2013.01); *C08K 5/01* (2013.01); *C08L 63/00* (2013.01); *C09D 163/00* (2013.01); *C09J 163/00* (2013.01)

(58) Field of Classification Search
CPC ...... C07K 2317/60–66; C07K 2318/31; C07K 2316/52; C07K 2317/31; C07K 16/468
See application file for complete search history.

(56) References Cited

U.S. PATENT DOCUMENTS

| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbus et al. |
| 5,661,016 A | 8/1997 | Lonberg et al. |
| 5,667,425 A | 9/1997 | Pineau et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |

(Continued)

FOREIGN PATENT DOCUMENTS

| EP | 0392745 | 10/1990 |
| EP | 0438474 | 7/1991 |

(Continued)

OTHER PUBLICATIONS

George & Huston, Chapter 6, pp. 99-141, "Bispecific Antibody Engineering" in The Antibodies, Harwood Academic Publishers, eds. M. Zanetti & J. D. Capra, vol. 4, 1997.*
Hudson and Kortt, J Immunol Methods 1999; 231:177-89.*
Webber et al., Mol Immunol. 1995; 32(4):249-58.*
Ames et al., J Immunol Meth 1995; 184:177-86.*
Reiter et al., J Biol Chem 1994; 269:18327-331.*
Kohler, et al. Nature, 256:495-497 (1975).
Kozbor, et al., Immunology Today, 4:72 (1983).
Cole, et al., Monoclonal Antibodies and Cancer Therapy, pp. 77-96 (1985).
Babcook, J., et al. Proc. Natl. Acad. Sci., 93:7843-7848 (1996).
Brinkman, et al., J. Immunol. Methods, 182:41-50 (1995).

(Continued)

*Primary Examiner* — Jessica H Roark

(74) *Attorney, Agent, or Firm* — McDonnell Boehnen Hulbert & Berghoff LLP

(57) ABSTRACT

The present disclosure provides a binding protein comprising: a polypeptide heavy chain comprising: $VH_1\text{-}(X_1)n\text{-}VH_2\text{---}CH\ (X_2)y$ wherein $VH_1$ is a first variable domain, $VH_2$ is a second variable domain, CH is a constant domain, $X_1$ represents an amino acid or peptide, $X_2$ represents an Fc region, n is 0 or 1 and y is independently 1 or 2, and a polypeptide light chain comprising: $VL_1\text{-}(X_1)n\text{-}VL_2\text{-}C$ wherein VL1 is a first variable domain, $VL_2$ is a second variable domain, C is a constant domain, $X_1$ represents an amino acid or peptide and n is 0 or 1, wherein the heavy chain and light chain are aligned such that $VH_1$ and $VL_1$ form a first binding domain, and $VH_2$ and $VL_2$ form a second binding domain and wherein: there is a disulfide bond between $VH_1$ and $VL_1$, and/or there is a disulfide bond between $VH_2$ and $VL_2$, and use thereof in treatment.

6 Claims, 6 Drawing Sheets
Specification includes a Sequence Listing.

(56) References Cited

U.S. PATENT DOCUMENTS

| | | | |
|---|---|---|---|
| 5,770,429 | A | 6/1998 | Lonberg et al. |
| 5,780,225 | A | 7/1998 | Wigler et al. |
| 5,821,047 | A | 10/1998 | Garrard et al. |
| 5,969,108 | A | 10/1999 | McCafferty et al. |
| 5,989,830 | A * | 11/1999 | Davis et al. .................... 435/7.1 |
| 6,331,415 | B1 | 12/2001 | Cabilly et al. |
| 6,642,356 | B1 | 11/2003 | Humphreys |
| 2004/0220388 | A1 | 11/2004 | Mertens et al. |
| 2009/0155275 | A1* | 6/2009 | Wu et al. .................... 424/136.1 |
| 2009/0252729 | A1* | 10/2009 | Farrington et al. ........ 424/135.1 |

FOREIGN PATENT DOCUMENTS

| | | |
|---|---|---|
| EP | 0463151 | 1/1992 |
| EP | 0546073 B1 | 6/1993 |
| WO | WO8601533 | 3/1986 |
| WO | WO9002809 | 3/1990 |
| WO | WO9109967 | 7/1991 |
| WO | WO9110737 | 7/1991 |
| WO | WO9201047 | 1/1992 |
| WO | WO9202551 | 2/1992 |
| WO | WO9218619 | 10/1992 |
| WO | WO9222583 | 12/1992 |
| WO | WO9306231 | 4/1993 |
| WO | WO9311236 | 6/1993 |
| WO | WO9515982 | 6/1995 |
| WO | WO9520401 | 8/1995 |
| WO | WO9820734 | 5/1998 |
| WO | WO9825971 | 6/1998 |
| WO | WO8900195 | 1/1999 |
| WO | WO8901476 | 2/1999 |
| WO | WO9915549 | 4/1999 |
| WO | WO03031581 | 4/2003 |
| WO | WO2004051268 | 6/2004 |
| WO | WO2005003169 | 1/2005 |
| WO | WO2005003170 | 1/2005 |
| WO | WO2005003171 | 1/2005 |
| WO | WO05117984 | 12/2005 |
| WO | WO2007024715 | 3/2007 |
| WO | WO2007/106120 A2 * | 9/2007 |
| WO | WO2007106120 | 9/2007 |
| WO | WO2004106377 | 12/2007 |
| WO | WO2008/024188 A2 * | 2/2008 |
| WO | WO2008038024 | 4/2008 |
| WO | WO2008131242 | 10/2008 |
| WO | WO2011/030107 A1 * | 3/2011 |

OTHER PUBLICATIONS

Kettleborough, et al., Eur. J.Immunol., 24:952-958 (1994).
Persic, et al., Gene, 187:9-18 (1997).
Burton, et al., Advances in Immunology, 57:191-280 (1994).
Ward, et al., Nature, 341:544 (1989).
Orlandi, et al., Proc. Natl. Acad. Sci., 86:3833 (1989).
Riechmann, et al., Nature, 322:323 (1988).
Bird, et al., Science, 242:423 (1988).
Mountain, et al., Biotechnol. Genet. Eng. Rev., 10:1-142 (1992).
Verma, et al., Journal of Immunological Methods, 216:165-181 (1998).
Wu, et al., MABS, 1:339-347 (2009).
Huang, et al., Journal of Immunological Methods, 313:149-160 (2006).
Reiter, et al., Journal of Biological Chemistry, 269:18327-18331 (1994).
Rajagopal, et al., Protein Engineering, 10:1453-1459 (1997).
Luo, et al., J. Biochem., 118:825-831 (1995).
Young, et al., FEBS Letters, 377:135-139 (1995).
Glockshuber, et al., Biochemistry, 29:1362-1367 (1990).
Brinkmann, et al., Proc. Natl. Acad. Sci., 90:7538-7542 (1993).
Jung, et al., Proteins, 19:35-47 (1994).
Wells, et al., Gene, 34:315-323 (1985).
Angal, et al., Molecular Immunology, 30:105-108 (1993).
Harris, R.J., Journal of Chromatography, 705:129-134 (1995).
Hellstrom, et al., Controlled Drug Delivery, pp. 623-653 (1987).
Thorpe, et al., Immunol. Rev., 62:119-58 (1982).
Dubowchik, et al., Pharmacology and Therapeutics, 83:67-123 (1999).
Chapman, Advanced Drug Delivery Reviews, 54:531-545 (2002).
Zhu, et al, Protein Science, 6:781-788 (1997).
Reiter, et al., Nature Biotechnology, 14:1239-1245 (1996).
Wu, et al., Nature Biotechnology, 25:1290-1297 (2007).
Weatherill et al., "Towards a universal disulphide stabilised single chain Fv format: importance of interchain disulphide bond location and vL-vH orientation", Protein Engineering, Design & Selection pp. 1-9, 1, 2012).
Brinkmann "Disulfide-Stabilized Fv Fragments" Antibody Engineering, 181-189, 182 (2010).
Bird et al. Science, 242, 423-426 (1988).
Huston et al. Proc. Natl. Acad. Sci. U S A, 85, 5879-5883 (1988).
Skerra A, Pluckthun A (1988) Assembly of a functional immunoglobulin Fv fragment in *Escherichia coli*. Science 240:1038-1041.
Glockshuber R, Malia M, Pfitzinger I, Pluckthun A (1990) A comparison of strategies to stabilize immunoglobulin Fv-fragments. Biochemistry 29:1362-1367.
Rothlisberger et al., Domain Interactions in the Fab Fragment: A comparative Evaluation of the Single-chain Fv and the Fab Format Engineered with Variable Domains of Different Stability, J Mol Biol. 347, 773-789, 786 (2005).
Reiter Y, Brinkmann U, Lee B, Pastan I (1996) Engineering antibody Fv fragments for cancer detection and therapy: disulfide-stabilized Fv fragments. Nature Biotechnol 14(10):1239-1245. PMID:9631086.
Chan & Carter, "Therapeutic antibodies for autoimmunity and inflammation," Nat Rev Immunol. 10(5):301-16 (May 2010).
Klein et al., "Progress in overcoming the chain association issue in bispecific heterodimeric IgG antibodies," MAbs 4 (6):653-63 (Nov. 2012).
Reiter et al., "Stabilization of the Fv fragments in recombinant immunotoxins by disulfide bonds engineered into conserved framework regions," Biochemistry 33(18):5451-9 (May 1994).
Orcutt et al., "A modular IgG-scFv bispecific antibody topology", Protein Engineering, Design & Selection, 23:221-228 (2010).

* cited by examiner

SEQUENCE LISTING

```
<160> NUMBER OF SEQ ID NOS: 97

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Lys Thr His Thr Cys Ala Ala
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Asp Lys Thr His Thr Cys Pro Pro Cys Pro Ala
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Asp Lys Thr His Thr Cys Pro Pro Cys Pro Ala Thr Cys Pro Pro Cys
1               5                   10                  15

Pro Ala

<210> SEQ ID NO 4
<211> LENGTH: 25
<212> TYPE: PRT
<213> ORGANISM: Artificial Sequence
<220> FEATURE:
<223> OTHER INFORMATION: Synthetic

<400> SEQUENCE: 4

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25
```

<210> SEQ ID NO 5
<211> LENGTH: 30
<212> TYPE: PRT
<213> ORGANISM: Artificial Sequence
<220> FEATURE:
<223> OTHER INFORMATION: Synthetic

<400> SEQUENCE: 5

Asp Lys Thr His Thr Cys Pro Pro Cys Pro Ala Gly Lys Pro Thr Leu
1               5                   10                  15
Tyr Asn Ser Leu Val Met Ser Asp Thr Ala Gly Thr Cys Tyr
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic

<400> SEQUENCE: 6

Asp Lys Thr His Thr Cys Pro Pro Cys Pro Ala Gly Lys Pro Thr His
1               5                   10                  15
Val Asn Val Ser Val Val Met Ala Glu Val Asp Gly Thr Cys Tyr
            20                  25                  30

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Asp Lys Thr His Thr Cys Cys Val Glu Cys Pro Pro Cys Pro Ala
1               5                   10                  15

<210> SEQ ID NO 8
<211> LENGTH: 26
<212> TYPE: PRT
<213> ORGANISM: Artificial Sequence
<220> FEATURE:
<223> OTHER INFORMATION: Synthetic

<400> SEQUENCE: 8

Asp Lys Thr His Thr Cys Pro Arg Cys Pro Glu Pro Lys Ser Cys Asp
1               5                   10                  15
Thr Pro Pro Pro Cys Pro Arg Cys Pro Ala
            20                  25

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Asp Lys Thr His Thr Cys Pro Ser Cys Pro Ala
1               5                   10

<210> SEQ ID NO 10
<211> LENGTH: 7
<212> TYPE: PRT
<213> ORGANISM: Artificial Sequence

```
<220> FEATURE:
<223> OTHER INFORMATION: Synthetic

<400> SEQUENCE: 10

Ser Gly Gly Gly Gly Ser Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Asp Lys Thr His Thr Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Ser Gly Gly Gly Gly Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Ser Gly Gly Gly Gly Ser Gly Gly Gly Gly Ser
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic

<400> SEQUENCE: 14

Ser Gly Gly Gly Gly Ser Gly Gly Gly Gly Ser Gly Gly Gly Gly Ser
1               5                   10                  15

<210> SEQ ID NO 15
<211> LENGTH: 21
<212> TYPE: PRT
<213> ORGANISM: Artificial Sequence
<220> FEATURE:
<223> OTHER INFORMATION: Synthetic

<400> SEQUENCE: 15

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 16
<211> LENGTH: 26
```

```
<212> TYPE: PRT
<213> ORGANISM: Artificial Sequence
<220> FEATURE:
<223> OTHER INFORMATION: Synthetic

<400> SEQUENCE: 16

Ser Gly Gly Gly Gly Ser Gly Gly Gly Ser Gly Gly Gly Ser
1               5                   10                  15

Gly Gly Gly Gly Ser Gly Gly Gly Gly Ser
            20                  25

<210> SEQ ID NO 17
<211> LENGTH: 11
<212> TYPE: PRT
<213> ORGANISM: Artificial Sequence
<220> FEATURE:
<223> OTHER INFORMATION: Synthetic

<400> SEQUENCE: 17

Ala Ala Ala Gly Ser Gly Gly Ala Ser Ala Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 18

Ala Ala Ala Gly Ser Gly Xaa Gly Gly Gly Ser Gly Ala Ser Ala Ser
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 19

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 20
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
```

<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 20

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 21
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 21

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 22
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Ala Ala Ala Gly Ser Gly Xaa Ser Gly Ala Ser Ala Ser
1               5                   10

<210> SEQ ID NO 23
<211> LENGTH: 28
<212> TYPE: PRT
<213> ORGANISM: Artificial Sequence
<220> FEATURE:
<223> OTHER INFORMATION: Synthetic

<400> SEQUENCE: 23

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Ala Thr Thr Thr Gly Ser Ser Pro Gly Pro Thr
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Ala Thr Thr Thr Gly Ser
1               5

<210> SEQ ID NO 26
<211> LENGTH: 21
<212> TYPE: PRT
<213> ORGANISM: Artificial Sequence
<220> FEATURE:
<223> OTHER INFORMATION: Synthetic

<400> SEQUENCE: 26

Glu Pro Ser Gly Pro Ile Ser Thr Ile Asn Ser Pro Ser Lys Glu
1               5                   10                  15

Ser His Lys Ser Pro
            20

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Gly Thr Val Ala Ala Pro Ser Val Phe Ile Phe Pro Pro Ser Asp
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Gly Gly Gly Gly Ile Ala Pro Ser Met Val Gly Gly Gly Gly Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

```
Gly Gly Gly Gly Lys Val Glu Gly Ala Gly Gly Gly Gly Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Gly Gly Gly Gly Ser Met Lys Ser His Asp Gly Gly Gly Gly Ser
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Gly Gly Gly Gly Asn Leu Ile Thr Ile Val Gly Gly Gly Gly Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Gly Gly Gly Gly Val Val Pro Ser Leu Pro Gly Gly Gly Gly Ser
1               5                   10                  15

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Gly Gly Glu Lys Ser Ile Pro Gly Gly Gly Gly Ser
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthetic

<400> SEQUENCE: 34

Arg Pro Leu Ser Tyr Arg Pro Pro Phe Pro Phe Gly Phe Pro Ser Val
1               5                   10                  15

Arg Pro

<210> SEQ ID NO 35
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 35

Tyr Pro Arg Ser Ile Tyr Ile Arg Arg His Pro Ser Pro Ser Leu
1               5                   10                  15

Thr Thr

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Thr Pro Ser His Leu Ser His Ile Leu Pro Ser Phe Gly Leu Pro Thr
1               5                   10                  15

Phe Asn

<210> SEQ ID NO 37
<211> LENGTH: 18
<212> TYPE: PRT
<213> ORGANISM: Artificial Sequence
<220> FEATURE:
<223> OTHER INFORMATION: Synthetic

<400> SEQUENCE: 37

Arg Pro Val Ser Pro Phe Thr Phe Pro Arg Leu Ser Asn Ser Trp Leu
1               5                   10                  15

Pro Ala

<210> SEQ ID NO 38
<211> LENGTH: 18
<212> TYPE: PRT
<213> ORGANISM: Artificial Sequence
<220> FEATURE:
<223> OTHER INFORMATION: Synthetic

<400> SEQUENCE: 38

Ser Pro Ala Ala His Phe Pro Arg Ser Ile Pro Arg Pro Gly Pro Ile
1               5                   10                  15

Arg Thr

<210> SEQ ID NO 39
<211> LENGTH: 18
<212> TYPE: PRT
<213> ORGANISM: Artificial Sequence
<220> FEATURE:
<223> OTHER INFORMATION: Synthetic

<400> SEQUENCE: 39

Ala Pro Gly Pro Ser Ala Pro Ser His Arg Ser Leu Pro Ser Arg Ala
1               5                   10                  15

Phe Gly

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Pro Arg Asn Ser Ile His Phe Leu His Pro Leu Leu Val Ala Pro Leu
1               5                   10                  15
```

Gly Ala

<210> SEQ ID NO 41
<211> LENGTH: 18
<212> TYPE: PRT
<213> ORGANISM: Artificial Sequence
<220> FEATURE:
<223> OTHER INFORMATION: Synthetic

<400> SEQUENCE: 41

Met Pro Ser Leu Ser Gly Val Leu Gln Val Arg Tyr Leu Ser Pro Pro
1               5                   10                  15

Asp Leu

<210> SEQ ID NO 42
<211> LENGTH: 18
<212> TYPE: PRT
<213> ORGANISM: Artificial Sequence
<220> FEATURE:
<223> OTHER INFORMATION: Synthetic

<400> SEQUENCE: 42

Ser Pro Gln Tyr Pro Ser Pro Leu Thr Leu Thr Leu Pro Pro His Pro
1               5                   10                  15

Ser Leu

<210> SEQ ID NO 43
<211> LENGTH: 18
<212> TYPE: PRT
<213> ORGANISM: Artificial Sequence
<220> FEATURE:
<223> OTHER INFORMATION: Synthetic

<400> SEQUENCE: 43

Asn Pro Ser Leu Asn Pro Pro Ser Tyr Leu His Arg Ala Pro Ser Arg
1               5                   10                  15

Ile Ser

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Leu Pro Trp Arg Thr Ser Leu Leu Pro Ser Leu Pro Leu Arg Arg Arg
1               5                   10                  15

Pro

<210> SEQ ID NO 45
<211> LENGTH: 18
<212> TYPE: PRT
<213> ORGANISM: Artificial Sequence
<220> FEATURE:
<223> OTHER INFORMATION: Synthetic

<400> SEQUENCE: 45

Pro Pro Leu Phe Ala Lys Gly Pro Val Gly Leu Leu Ser Arg Ser Phe
1               5                   10                  15

Pro Pro

```
<210> SEQ ID NO 46
<211> LENGTH: 18
<212> TYPE: PRT
<213> ORGANISM: Artificial Sequence
<220> FEATURE:
<223> OTHER INFORMATION: Synthetic

<400> SEQUENCE: 46

Val Pro Pro Ala Pro Val Val Ser Leu Arg Ser Ala His Ala Arg Pro
1               5                   10                  15

Pro Tyr

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Leu Arg Pro Thr Pro Pro Arg Val Arg Ser Tyr Thr Cys Cys Pro Thr
1               5                   10                  15

Pro

<210> SEQ ID NO 48
<211> LENGTH: 18
<212> TYPE: PRT
<213> ORGANISM: Artificial Sequence
<220> FEATURE:
<223> OTHER INFORMATION: Synthetic

<400> SEQUENCE: 48

Pro Asn Val Ala His Val Leu Pro Leu Leu Thr Val Pro Trp Asp Asn
1               5                   10                  15

Leu Arg

<210> SEQ ID NO 49
<211> LENGTH: 18
<212> TYPE: PRT
<213> ORGANISM: Artificial Sequence
<220> FEATURE:
<223> OTHER INFORMATION: Synthetic

<400> SEQUENCE: 49

Cys Asn Pro Leu Leu Pro Leu Cys Ala Arg Ser Pro Ala Val Arg Thr
1               5                   10                  15

Phe Pro

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Ala Lys Thr Thr Pro Lys Leu Glu Glu Gly Glu Phe Ser Glu Ala Arg
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 51

Ala Lys Thr Thr Pro Lys Leu Glu Glu Gly Glu Phe Ser Glu Ala Arg
1               5                   10                  15
Val

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Ala Lys Thr Thr Pro Lys Leu Gly Gly
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Ser Ala Lys Thr Thr Pro Lys Leu Gly Gly
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Ala Lys Thr Thr Pro Lys Leu Glu Glu Gly Glu Phe Ser Glu Ala Arg
1               5                   10                  15
Val

<210> SEQ ID NO 55
<211> LENGTH: 6
<212> TYPE: PRT
<213> ORGANISM: Artificial Sequence
<220> FEATURE:
<223> OTHER INFORMATION: Synthetic

<400> SEQUENCE: 55

Ser Ala Lys Thr Thr Pro
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

Ser Ala Lys Thr Thr Pro Lys Leu Gly Gly
1               5                   10

<210> SEQ ID NO 57
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 57

Arg Ala Asp Ala Ala Pro
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Arg Ala Asp Ala Ala Pro Thr Val Ser
1               5

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Arg Ala Asp Ala Ala Ala Ala Gly Gly Pro Gly Ser
1               5                   10

<210> SEQ ID NO 60
<211> LENGTH: 27
<212> TYPE: PRT
<213> ORGANISM: Artificial Sequence
<220> FEATURE:
<223> OTHER INFORMATION: Synthetic

<400> SEQUENCE: 60

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 61
<211> LENGTH: 18
<212> TYPE: PRT
<213> ORGANISM: Artificial Sequence
<220> FEATURE:
<223> OTHER INFORMATION: Synthetic

<400> SEQUENCE: 61

Ser Ala Lys Thr Thr Pro Lys Leu Glu Glu Gly Glu Phe Ser Glu Ala
1               5                   10                  15

Arg Val

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

Ala Asp Ala Ala Pro
1               5
```

```
<210> SEQ ID NO 63
<211> LENGTH: 12
<212> TYPE: PRT
<213> ORGANISM: Artificial Sequence
<220> FEATURE:
<223> OTHER INFORMATION: Synthetic

<400> SEQUENCE: 63

Ala Asp Ala Ala Pro Thr Val Ser Ile Phe Pro Pro
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Synthetic

<400> SEQUENCE: 64

Thr Val Ala Ala Pro
1               5

<210> SEQ ID NO 65
<211> LENGTH: 12
<212> TYPE: PRT
<213> ORGANISM: Artificial Sequence
<220> FEATURE:
<223> OTHER INFORMATION: Synthetic

<400> SEQUENCE: 65

Thr Val Ala Ala Pro Ser Val Phe Ile Phe Pro Pro
1               5                   10

<210> SEQ ID NO 66
<211> LENGTH: 6
<212> TYPE: PRT
<213> ORGANISM: Artificial Sequence
<220> FEATURE:
<223> OTHER INFORMATION: Synthetic

<400> SEQUENCE: 66

Gln Pro Lys Ala Ala Pro
1               5

<210> SEQ ID NO 67
<211> LENGTH: 13
<212> TYPE: PRT
<213> ORGANISM: Artificial Sequence
<220> FEATURE:
<223> OTHER INFORMATION: Synthetic

<400> SEQUENCE: 67

Gln Pro Lys Ala Ala Pro Ser Val Thr Leu Phe Pro Pro
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

Ala Lys Thr Thr Pro Pro
1               5
```

```
<210> SEQ ID NO 69
<211> LENGTH: 13
<212> TYPE: PRT
<213> ORGANISM: Artificial Sequence
<220> FEATURE:
<223> OTHER INFORMATION: Synthetic

<400> SEQUENCE: 69

Ala Lys Thr Thr Pro Pro Ser Val Thr Pro Leu Ala Pro
1               5                   10

<210> SEQ ID NO 70
<211> LENGTH: 6
<212> TYPE: PRT
<213> ORGANISM: Artificial Sequence
<220> FEATURE:
<223> OTHER INFORMATION: Synthetic

<400> SEQUENCE: 70

Ala Lys Thr Thr Ala Pro
1               5

<210> SEQ ID NO 71
<211> LENGTH: 13
<212> TYPE: PRT
<213> ORGANISM: Artificial Sequence
<220> FEATURE:
<223> OTHER INFORMATION: Synthetic

<400> SEQUENCE: 71

Ala Lys Thr Thr Ala Pro Ser Val Tyr Pro Leu Ala Pro
1               5                   10

<210> SEQ ID NO 72
<211> LENGTH: 6
<212> TYPE: PRT
<213> ORGANISM: Artificial Sequence
<220> FEATURE:
<223> OTHER INFORMATION: Synthetic

<400> SEQUENCE: 72

Ala Ser Thr Lys Gly Pro
1               5

<210> SEQ ID NO 73
<211> LENGTH: 13
<212> TYPE: PRT
<213> ORGANISM: Artificial Sequence
<220> FEATURE:
<223> OTHER INFORMATION: Synthetic

<400> SEQUENCE: 73

Ala Ser Thr Lys Gly Pro Ser Val Phe Pro Leu Ala Pro
1               5                   10

<210> SEQ ID NO 74
<211> LENGTH: 15
<212> TYPE: PRT
<213> ORGANISM: Artificial Sequence
<220> FEATURE:
<223> OTHER INFORMATION: Synthetic

<400> SEQUENCE: 74

Gly Glu Asn Lys Val Glu Tyr Ala Pro Ala Leu Met Ala Leu Ser
1               5                   10                  15

<210> SEQ ID NO 75
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 75

Gly Pro Ala Lys Glu Leu Pro Leu Lys Glu Ala Lys Val Ser
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Synthetic

<400> SEQUENCE: 76

Gly His Glu Ala Ala Val Met Gln Val Gln Tyr Pro Ala Ser
1               5                   10                  15

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

Ser Ala Lys Thr Thr Pro
1               5

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Thr Val Ser Ser Ala Ser Thr Lys Gly Pro
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Glu Ile Lys Arg Thr Thr Val Ala Ala Pro Ser
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Asp Leu Cys Leu Arg Asp Trp Gly Cys Leu Trp
1               5                   10

<210> SEQ ID NO 81
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 81

Asp Ile Cys Leu Pro Arg Trp Gly Cys Leu Trp
1               5                   10

<210> SEQ ID NO 82
<211> LENGTH: 15
<212> TYPE: PRT
<213> ORGANISM: Artificial Sequence
<220> FEATURE:
<223> OTHER INFORMATION: Synthetic

<400> SEQUENCE: 82

Met Glu Asp Ile Cys Leu Pro Arg Trp Gly Cys Leu Trp Gly Asp
1               5                   10                  15

<210> SEQ ID NO 83
<211> LENGTH: 20
<212> TYPE: PRT
<213> ORGANISM: Artificial Sequence
<220> FEATURE:
<223> OTHER INFORMATION: Synthetic

<400> SEQUENCE: 83

Gln Arg Leu Met Glu Asp Ile Cys Leu Pro Arg Trp Gly Cys Leu Trp
1               5                   10                  15

Glu Asp Asp Glu
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic

<400> SEQUENCE: 84

Gln Gly Leu Ile Gly Asp Ile Cys Leu Pro Arg Trp Gly Cys Leu Trp
1               5                   10                  15

Gly Arg Ser Val
            20

<210> SEQ ID NO 85
<211> LENGTH: 21
<212> TYPE: PRT
<213> ORGANISM: Artificial Sequence
<220> FEATURE:
<223> OTHER INFORMATION: Synthetic

<400> SEQUENCE: 85

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 86
<211> LENGTH: 15
<212> TYPE: PRT
<213> ORGANISM: Artificial Sequence
<220> FEATURE:
<223> OTHER INFORMATION: Synthetic
```

<400> SEQUENCE: 86

Glu Asp Ile Cys Leu Pro Arg Trp Gly Cys Leu Trp Glu Asp Asp
1               5                   10                  15

<210> SEQ ID NO 87
<211> LENGTH: 18
<212> TYPE: PRT
<213> ORGANISM: Artificial Sequence
<220> FEATURE:
<223> OTHER INFORMATION: Synthetic

<400> SEQUENCE: 87

Arg Leu Met Glu Asp Ile Cys Leu Pro Arg Trp Gly Cys Leu Trp Glu
1               5                   10                  15

Asp Asp

<210> SEQ ID NO 88
<211> LENGTH: 16
<212> TYPE: PRT
<213> ORGANISM: Artificial Sequence
<220> FEATURE:
<223> OTHER INFORMATION: Synthetic

<400> SEQUENCE: 88

Met Glu Asp Ile Cys Leu Pro Arg Trp Gly Cys Leu Trp Glu Asp Asp
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

Met Glu Asp Ile Cys Leu Pro Arg Trp Gly Cys Leu Trp Glu Asp
1               5                   10                  15

<210> SEQ ID NO 90
<211> LENGTH: 18
<212> TYPE: PRT
<213> ORGANISM: Artificial Sequence
<220> FEATURE:
<223> OTHER INFORMATION: Synthetic

<400> SEQUENCE: 90

Arg Leu Met Glu Asp Ile Cys Leu Ala Arg Trp Gly Cys Leu Trp Glu
1               5                   10                  15

Asp Asp

<210> SEQ ID NO 91
<211> LENGTH: 20
<212> TYPE: PRT
<213> ORGANISM: Artificial Sequence
<220> FEATURE:
<223> OTHER INFORMATION: Synthetic

<400> SEQUENCE: 91

Glu Val Arg Ser Phe Cys Thr Arg Trp Pro Ala Glu Lys Ser Cys Lys
1               5                   10                  15

Pro Leu Arg Gly
            20

<210> SEQ ID NO 92

<210> SEQ ID NO 92
<211> LENGTH: 20
<212> TYPE: PRT
<213> ORGANISM: Artificial Sequence
<220> FEATURE:
<223> OTHER INFORMATION: Synthetic

<400> SEQUENCE: 92

Arg Ala Pro Glu Ser Phe Val Cys Tyr Trp Glu Thr Ile Cys Phe Glu
1               5                   10                  15

Arg Ser Glu Gln
            20

<210> SEQ ID NO 93
<211> LENGTH: 11
<212> TYPE: PRT
<213> ORGANISM: Artificial Sequence
<220> FEATURE:
<223> OTHER INFORMATION: Synthetic

<400> SEQUENCE: 93

Glu Met Cys Tyr Phe Pro Gly Ile Cys Trp Met
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic

<400> SEQUENCE: 94

Gly Ala Pro Ala Pro Ala Ala Pro Ala Pro Ala
1               5                   10

<210> SEQ ID NO 95
<211> LENGTH: 4
<212> TYPE: PRT
<213> ORGANISM: Artificial Sequence
<220> FEATURE:
<223> OTHER INFORMATION: Synthetic

<400> SEQUENCE: 95

Pro Pro Pro Pro
1

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Glu Ile Lys Arg Thr Val Ala Ala Pro Ser
1               5                   10

<210> SEQ ID NO 97
<211> LENGTH: 6
<212> TYPE: PRT
<213> ORGANISM: Artificial Sequence
<220> FEATURE:
<223> OTHER INFORMATION: Synthetic

<400> SEQUENCE: 97

Arg Thr Val Ala Ala Pro
1               5

DISULFIDE STABILIZED DVD-IG MOLECULES

The present disclosure relates to antibodies with two antigen binding sites in a format with suitable stability and which can be expressed at suitable levels to be commercially viable.

Multivalent antibodies are known. However, even though the basic concept was disclosed a number of years ago, there have been practical difficulties associated with exploiting the technology and thus it has not been widely adopted for the preparation of pharmaceutical biologic products in development.

A non-natural/non-native antibody format can be very difficult to express, which may significantly increase the cost of goods to an untenable level. The formats may increase the immunogenicity or reduce the in vivo stability in comparison to a standard antibody or fragment and/or may have undesirable pharmokinetics.

In particular, the problems associated with preparing homogenous products have been a concern for non-natural formats. If, for example, there is more than one permutation for combining the component monomers then mixtures can result. Thus elaborate purification methods may be required to isolate the desired/target entity at satisfactory purity levels.

This has been addressed in a number of ways, for example using short linkers in the production of bispecific diabodies was said to aid appropriate dimerisation. However, data has shown that the orientation of the variable domains can influence expression of the format and the formation of active binding sites.

One approach to force the assembly in the desired arrangement or orientation is referred to as the "knob-in-hole" method, in which a large "knob" is introduced in the VH domain by, for example in some antibodies exchanging valine 137 with the large residue phenyl alanine and replacing leucine 45 with tryptophan. A complementary hole can be introduced, for example in the VL domain by, in some antibodies, mutating phenylalanine 98 to methionine and tryptophan 87 to alanine. However, reduced antigen-binding activity was observed for several constructs.

WO2007/024715 tries to address one or more of these problems by providing a multivalent multispecific antibody (DVD-Ig) of the type shown in FIG. 1. The DVD-Igs are characterized in that the variable domain of the Va is linked directly to the variable domain Vb, for example by an amino acid or peptide.

These formats after expression may form soluble aggregates in liquid carriers which can be problematic when formulating a biotherapeutic agent.

The present invention provides a stable multivalent format, which is thought to be capable of expression in a host and with a suitable stability profile.

Thus there is provided a binding protein comprising:
a polypeptide heavy chain comprising:

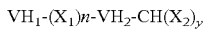

$VH_1\text{-}(X_1)_n\text{-}VH_2\text{-}CH(X_2)_y$ wherein $VH_1$ is a first variable domain, $VH_2$ is a second variable domain, CH is a constant domain, $X_1$ represents an amino acid or peptide, $X_2$ represents an Fc region, n is 0 or 1 and y is independently 1 or 2, and a polypeptide light chain comprising:

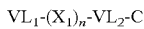

$VL_1\text{-}(X_1)_n\text{-}VL_2\text{-}C$ wherein $VL_1$ is a first variable domain, $VL_2$ is a second variable domain, C is a constant domain, $X_1$ represents an amino acid or peptide and n is 0 or 1, wherein the heavy chain and light chain are aligned such that $VH_1$ and $VL_1$ form a first binding domain, and $VH_2$ and $VL_2$ form a second binding domain and wherein:
there is a disulfide bond between $VH_1$ and $VL_1$, and/or there is a disulfide bond between $VH_2$ and $VL_2$.

The disulfide bond between $VH_1$ and $VL_1$ seems to aid general stability of the molecules. After expression and any purification this increased stability may, for example manifest itself in the absence of aggregation in liquid formulations of the antibody.

Figure 1:
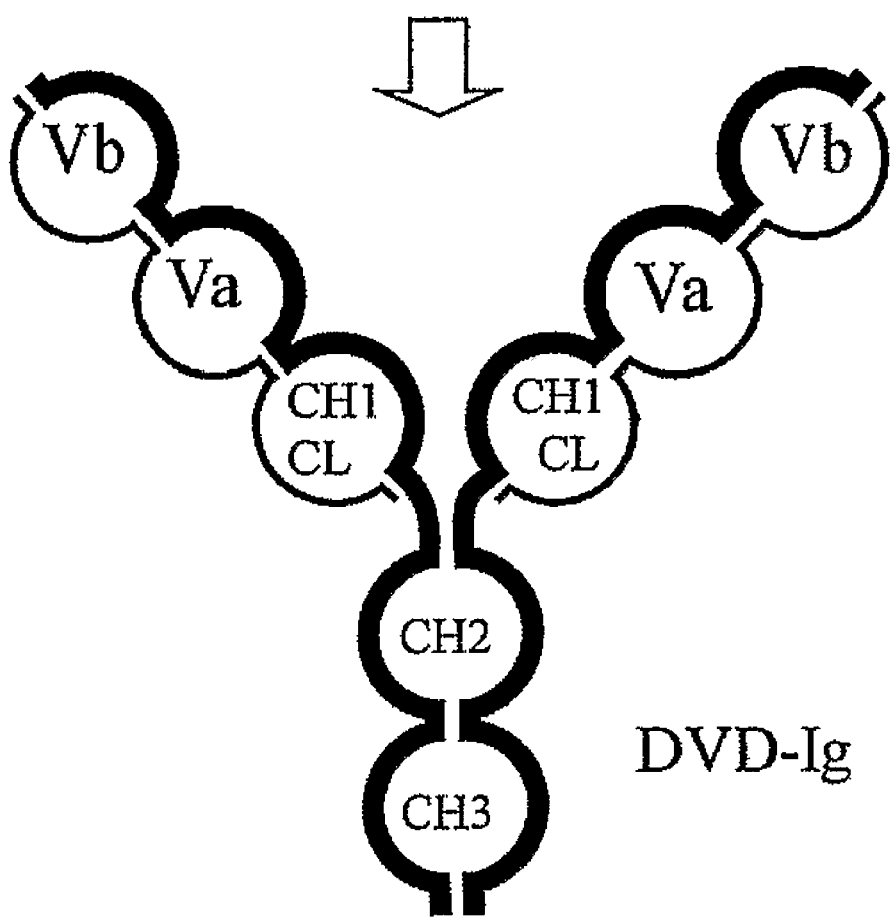
FIG. 1 shows a diagrammatic represents of a DVD-Ig molecule.
Figure 2:
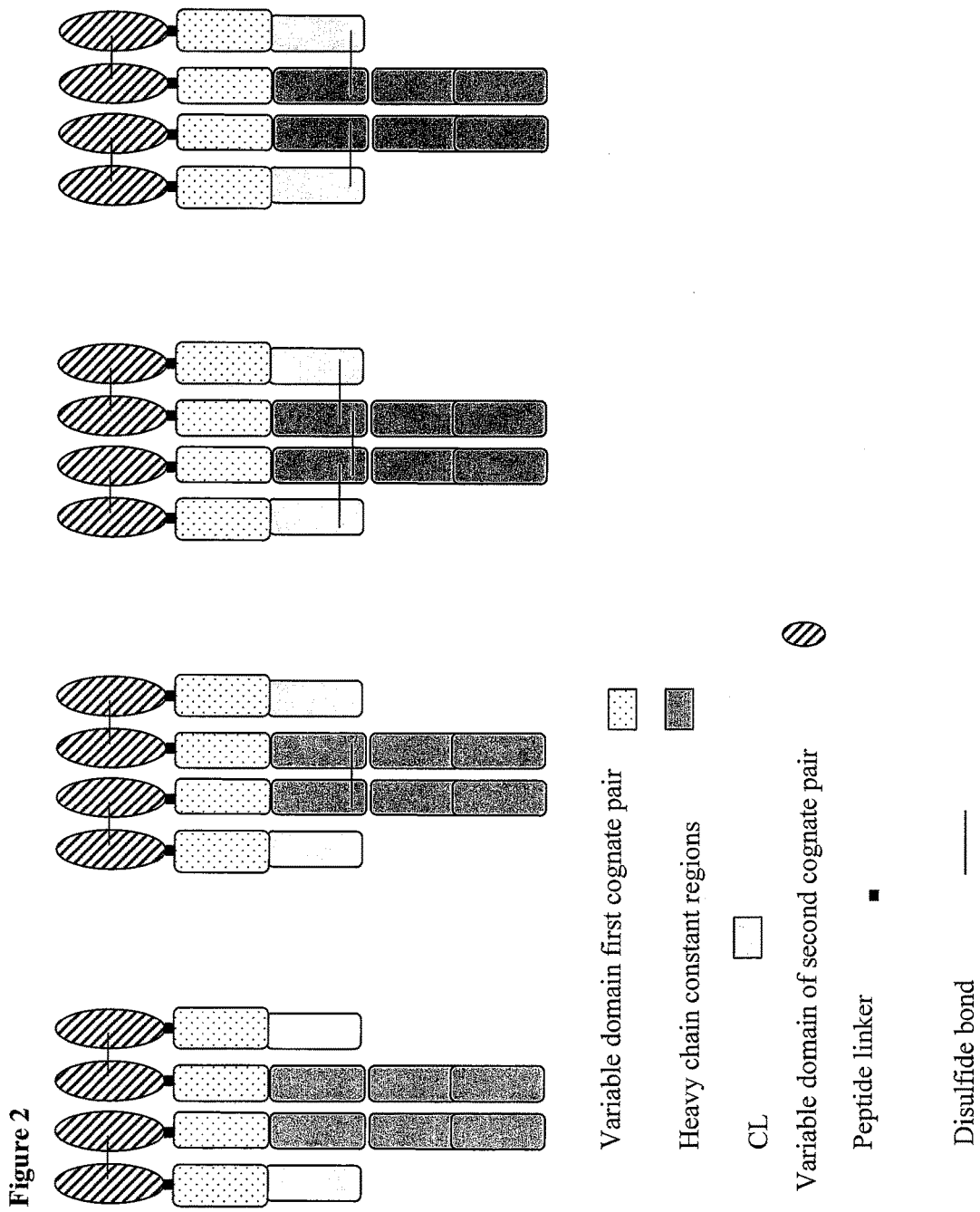
FIG. 2 to 4 shows various representations of a light and heavy chain format according to the present disclosure.
Figure 3:
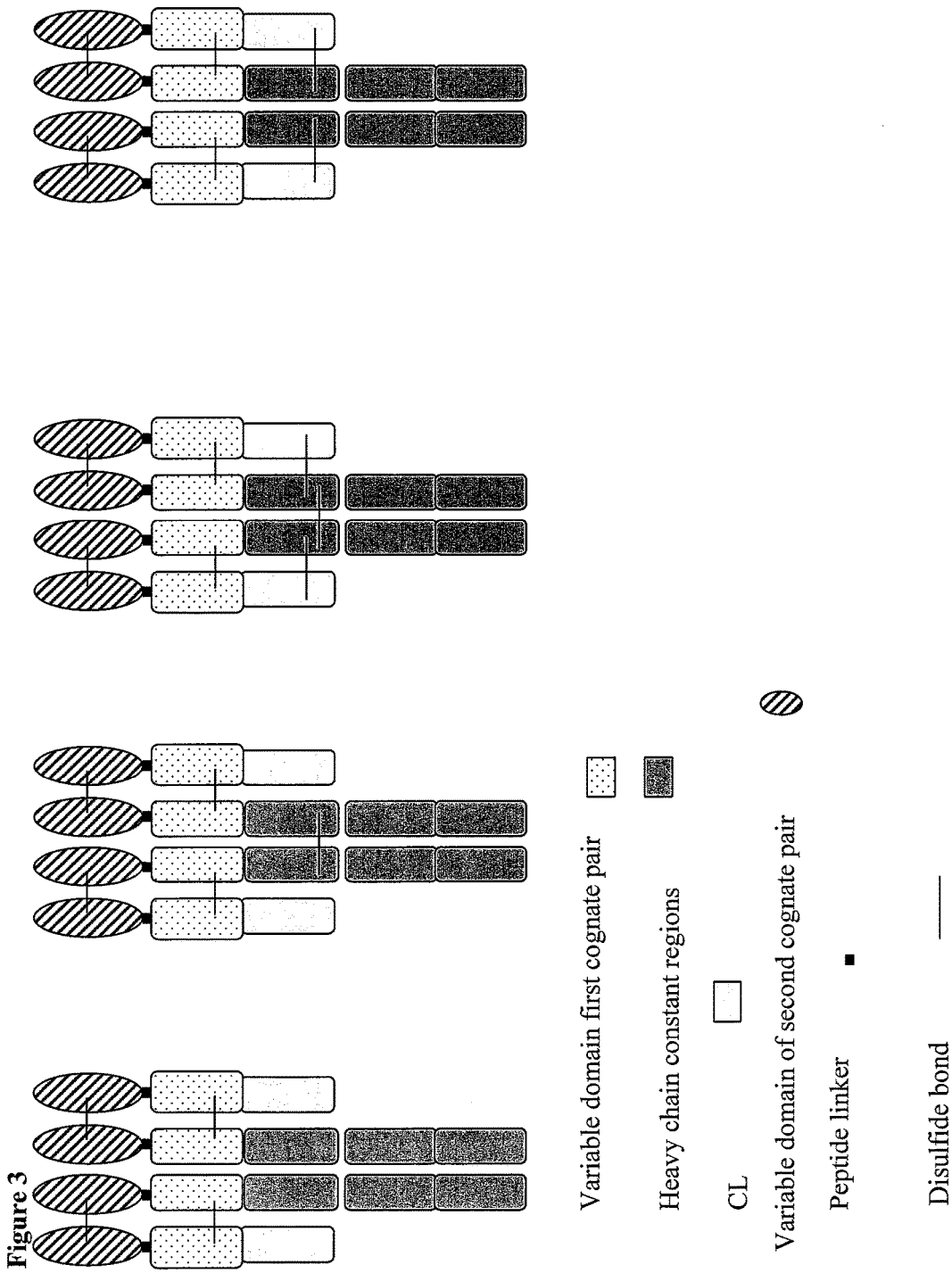
Figure 4:
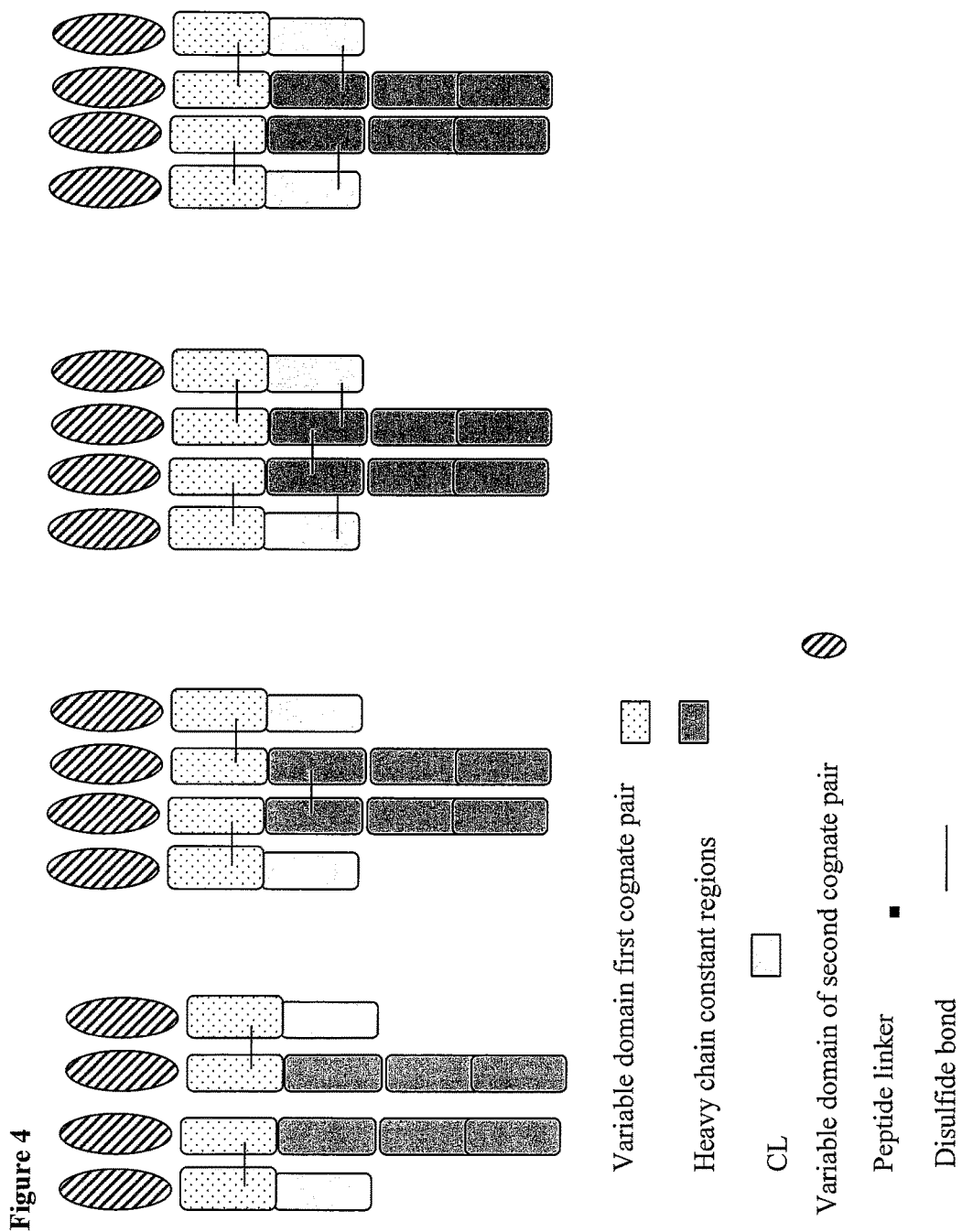

In one embodiment the variable domain pair has affinity for a target antigen of 100 nM or less, such as 50 nM or less, in particular 1 nM or less.

Suitable variable domain pairs may be identified by any means possible, for example including generation of antibodies in hosts and screening of B cells. Alternatively suitable pairs may be identified by phage display.

Components, such as variable domains for use in the present invention may be derived from antibodies or fragments thereof. The methods described below can be adapted to prepare molecules of the present invention.

Monoclonal antibodies may be prepared by any method known in the art such as the hybridoma technique (Kohler & Milstein, Nature, 1975, 256, 495-497), the trioma technique, the human B-cell hybridoma technique (Kozbor et al., Immunology Today, 1983, 4, 72) and the EBV-hybridoma technique (Cole et al., "Monoclonal Antibodies and Cancer Therapy", pp. 77-96, Alan R. Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al., Proc. Natl. Acad. Sci. USA, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

The antibodies can also be generated using various phage display methods known in the art and include those disclosed by Brinkman et al., J. Immunol. Methods, 1995, 182, 41-50; Ames et al., J. Immunol. Methods, 1995, 184, 177-186; Kettleborough et al. Eur. J. Immunol., 1994, 24, 952-958; Persic et al., Gene, 1997 187, 9-18; and Burton et al., Advances in Immunology, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. Nos. 5,545,806, 5,569,825, 5,625,126, 5,633,425, 5,661,016, 5,770,429, EP 0438474 B1 and EP0463151 B1.

A Fab or Fab' fragment starting material may be obtained from any whole antibody, especially a whole monoclonal antibody, using any suitable enzymatic cleavage and/or digestion techniques, for example by treatment with pepsin. Alternatively, or in addition the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

An antibody fragment may be obtained from any species including for example mouse, rat, rabbit, hamster, camel, llama, goat or human. Parts of the antibody fragment may be obtained from more than one species, for example the antibody fragments may be chimeric. In one example, the constant regions are from one species and the variable regions from another. The antibody fragment may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment each variable domain pair forming a binding domain is a cognate pair.

Cognate pair as employed herein is intended to refer to a natural pair of variable domains, that is to say isolated from a single antibody or antibody expressing cell.

In one example the cognate pair are a complementary VH/VL pair which bind the antigen co-operatively i.e. they are a complementary VH/VL pair.

Typically the cognate pair will be a VH/VL pair derived from the same antibody.

In one example the cognate pair are a pair of variable domains isolated as a pair from a 'library of pairs', such as a Fab phage display library.

In one example the VH/VL pair are monospecific.

Variable domains may have been optimized and/or humanized.

Optimised/humanized variable domains derived from a cognate pair will still be considered a cognate pair after optimization/humanization.

In one embodiment the disulfide bond between a variable region pair, for example $VH_1$ and $VL_1$ and/or $VH_2$ and $VL_2$ is between (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA:

VH37+VL95C see for example Protein Science 6, 781-788 Zhu et al (1997);

VH44+VL100 see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

VH44+VL105 see for example J Biochem. 118, 825-831 Luo et al (1995);

VH45+VL87 see for example Protein Science 6, 781-788 Zhu et al (1997);

VH55+VL101 see for example FEBS Letters 377 135-139 Young et al (1995);

VH100+VL50 see for example Biochemistry 29 1362-1367 Glockshuber et al (1990);

VH100b+VL49;

VH98+VL 46 see for example Protein Science 6, 781-788 Zhu et al (1997);

VH101+VL46;

VH105+VL43 see for example; Proc. Natl. Acad. Sci. USA Vol. 90 pp. 7538-7542 Brinkmann et al (1993); or Proteins 19, 35-47 Jung et al (1994), or VH106+VL57 see for example FEBS Letters 377 135-139 Young et al (1995)

or a position corresponding thereto in variable region pair located in the molecule.

The amino acid pairs listed above are in the positions conducive to replacement by cysteines such that disulfide bonds can be formed. Cysteines can be engineered into these desired positions by known techniques. In one embodiment therefore an engineered cysteine according to the present invention refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N Y, 1989; Ausbel et al., Current Protocols in Molecular Biology, Greene Publishing & Wiley-Interscience, N Y, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Accordingly in one embodiment a variable domain pair (VH/VL) of the present invention may be linked by a disulfide bond between two cysteine residues, one in VH and one in VL, wherein the position of the pair of cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57.

In one embodiment a variable domain pair (VH/VL) of the present invention may be linked by a disulfide bond between two cysteine residues, one in VH and one in VL, which are outside of the CDRs wherein the position of the pair of cysteine residues is selected from the group consisting of VH37 and VL95, VH44 and VL100, VH44 and VL105, VH45 and VL87, VH100 and VL50, VH98 and VL46, VH105 and VL43 and VH106 and VL57.

In one embodiment a variable domain pair (VH/VL) of the present invention may be linked by a disulfide bond between two cysteine residues, one in VH and one in VL, which are outside of the CDRs wherein the position of the pair of cysteine residues is selected from the group consisting of VH37 and VL95, VH44 and VL105, VH45 and VL87, VH100 and VL50, VH98 and VL46, VH105 and VL43 and VH106 and VL57.

In one embodiment a variable domain pair (VH/VL) of the present invention may be linked by a disulfide bond between two cysteine residues wherein the cysteine residue of VH is at position 44 and the cysteine residue of VL is at position 100.

Typically the cysteine pairs are engineered into those positions in VH and VL, accordingly in one embodiment a variable domain pair (VH/VL) of the present invention may be linked by a disulfide bond between two engineered cysteine residues, one in VH and one in VL, wherein the position of the pair of engineered cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57.

In one embodiment a variable domain pair (VH/VL) of the present invention may be linked by a disulfide bond between two engineered cysteine residues, one in VH and one in VL, which are outside of the CDRs wherein the position of the pair of engineered cysteine residues is selected from the group consisting of VH37 and VL95, VH44 and VL100, VH44 and VL105, VH45 and VL87, VH100 and VL50, VH98 and VL46, VH105 and VL43 and VH106 and VL57.

In one embodiment the variable domain pair (VH/VL) is linked by a disulfide bond between two engineered cysteine residues, one in VH and one in VL, which are outside of the CDRs wherein the position of the pair of engineered cysteine residues is selected from the group consisting of VH37 and VL95, VH44 and VL105, VH45 and VL87, VH100 and VL50, VH98 and VL46, VH105 and VL43 and VH106 and VL57.

In one embodiment the variable domain pair (VH/VL) is linked by a disulfide bond between two engineered cysteine residues wherein the engineered cysteine residue of VH is at position 44 and the engineered cysteine residue of VL is at position 100.

In one embodiment there is a disulfide bond between $VH_1$ and $VL_1$ only.

In one embodiment there is a disulfide bond between $VH_2$ and $VL_2$ only.

In one embodiment there is a disulfide bond between $VH_1$ and $VL_1$ and also a disulfide bond between $VH_2$ and $VL_2$.

In one embodiment the binding protein avidly binds the target antigen.

In one embodiment the binding protein according to the present disclosure is monospecific. Monospecific as employed herein is intended to refer to the fact that all the binding sites bind the same target antigen. In one aspect of this embodiment all the binding sites bind the same epitope(s) of said antigen. In an alternative embodiment at least two binding sites bind different epitopes on the target antigen.

In one embodiment the binding protein according to the present disclosure is bispecific such that two binding sites specifically bind different or distinct antigens.

Specifically binds as employed herein is intended to refer to antibodies have high affinity for a target antigen (to which it is specific) and which binds antigens to which it is not specific with a low or much lower affinity (or not at all). Methods of measuring affinity are known to those skilled in the art and include such assays as BIAcore.

The antibody molecules of the present invention suitably have a high binding affinity, in particular, nanomolar or picomolar. Affinity may be measured using any suitable method known in the art, including BIAcore. In one embodiment the antibody molecule of the present invention has a binding affinity of about 100 pM or better. In one embodiment the antibody molecule of the present invention has a binding affinity of about 50 pM or better. In one embodiment the antibody molecule of the present invention has a binding affinity of about 40 pM or better. In one embodiment the antibody molecule of the present invention has a binding affinity of about 30 pM or better. In one embodiment the antibody molecule of the present invention is fully human or humanised and has a binding affinity of about 100 pM or better.

"C" as employed herein refers to the constant region portion in the light chain, which may be a naturally occurring constant region (constant domain), for example a natural constant region derived from a light chain, e.g. kappa or lambda.

Constant domain as employed herein is intended to refer to $CH_1$, $CH_2$, $CH_3$ or a constant domain from a light chain.

In one embodiment CH is a $CH_1$ domain.

In one embodiment C is a constant domain from a light chain i.e. CL.

Fc as employed herein is a region comprising a constant domain.

In one embodiment the Fc region comprises domains —$CH_2CH_3$.

In one embodiment y is 1.
In one embodiment n is 1.
In one embodiment n is 0.

In one embodiment a "natural" disulfide bond is present between a $CH_1$ and CL. The CL domain is derived from either Kappa or Lambda. The natural position for a bond forming cysteine in the latter is 214 in human cKappa and cLambda (Kabat numbering 4th edition 1987). A disulfide bond or bond(s) in the constant region of the molecule are in addition to the at least one disulfide bond between a variable domain pair.

The exact location of the disulfide bond forming cysteine in $CH_1$ depends on the particular domain actually employed. Thus, for example in human gamma-1 the natural position of the disulfide bond is located position 233 (Kabat numbering 4th edition 1987). The position of the bond forming cysteine for other human isotypes such as gamma 2, 3, 4, IgM and IgD are known, for example 127.

In one embodiment the binding protein, according to the disclosure, has a disulfide bond in a position equivalent or corresponding to that in the naturally occurring CH and C such as CL.

In one embodiment a constant region comprising CH and a constant region such as CL has a disulfide bond which is in a non-naturally occurring position. This may be engineered into the molecule by introducing cysteine(s) into the amino acid chain at the positions required. This non-natural disulfide bond is in addition to or as an alternative to the natural disulfide bond present between CH and CL.

In one embodiment no disulfide bond between CH and CL is present, for example the interchain cysteines maybe replaced by another amino acid, such as serine.

In one or more embodiments herein there are no interchain disulfide bonds in the constant and/or Fc regions, for example the hinge region thereof.

Alternatively one or more embodiments herein may be provided with one or more (such as two) disulfide bonds in the constant and/or Fc regions, such as the hinge region thereof.

A disulfide bond(s) in the Fc region may, for example, be in an area approximately corresponding to the hinge region in natural antibodies.

Modified Fc regions may be employed, for example as disclosed in WO2008/131242.

In one embodiment the CH fragment, in the heavy chain, comprises a $CH_1$ domain. That is to say a naturally occurring domain 1 from a heavy chain or a derivative thereof. In one embodiment the CH fragment consists of a $CH_1$ domain.

In one embodiment the CL fragment, in the light chain, comprises a constant kappa sequence or a constant lambda sequence.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment the Fc region comprises $CH_2$ and/or $CH_3$ domains. In one embodiment the Fc fragment from the N-terminal is $-CH_2CH_3$. In an alternative embodiment the Fc region comprises or consists of from the N-terminal $-CH_2CH_3CH_2CH_3$. The latter may be provided with a linker between the middle $CH_3$ and $CH_2$ (such as $-CH_2CH_3$linker$CH_2CH_3$) to allow the terminal $CH_2CH_3$ flexibility to align with the first $CH_2CH_3$ (which is attached to the C terminal of the remainder of the molecule). This Fc arrangement may prolong half-life and/or allow flexibility to control/provide antibody fragments which are not cross-linking, if desired.

A number of modified hinge regions have already been described for example, in U.S. Pat. Nos. 5,677,425, 6,642,356, WO9915549, WO2005003170, WO2005003169, WO2005003170, WO9825971 and WO2005003171 and these are incorporated herein by reference. The hinge will usually be located (from the N-terminus) between the first and second constant domain in the heavy chain. Particular examples of hinges include those shown in Table 1.

TABLE 1

| SEQ ID NO: | Hinge linker sequences SEQUENCE |
|---|---|
| 1 | DKTHTCAA |
| 2 | DKTHTCPPCPA |

TABLE 1-continued

| SEQ ID NO: | Hinge linker sequences SEQUENCE |
|---|---|
| 3 | DKTHTCPPCPATCPPCPA |
| 4 | DKTHTCPPCPATCPPCPATCPPCPA |
| 5 | DKTHTCPPCPAGKPTLYNSLVMSDTAGTCY |
| 6 | DKTHTCPPCPAGKPTHVNVSVVMAEVDGTCY |
| 7 | DKTHTCCVECPPCPA |
| 8 | DKTHTCPRCPEPKSCDTPPPCPRCPA |
| 9 | DKTHTCPSCPA |

Thus in one embodiment the heavy and/or light chain comprises a modified hinge.

The modified hinges described above in Table 1 may also be used as linkers in other parts of the molecules, as required.

The arrangement of C in the light chain and $CH_1$ the constant region fragment in the heavy chain is thought to minimize inappropriate dimerisation.

The inventors believe that by providing variable domains as cognate pairs in the final construct optimizes and maintains the desirable antigen binding properties of the binding site formed by the relevant pair.

Examples of suitable peptide linkers are given below, for example in Table 2.

Suitable linkers for $X_1$ include:

TABLE 2

| SEQ ID NO: | Flexible linker sequences SEQUENCE |
|---|---|
| 10 | SGGGGSE |
| 11 | DKTHTS |
| 12 | (S)GGGGS |
| 13 | (S)GGGGSGGGGS |
| 14 | (S)GGGGSGGGGSGGGGS |
| 15 | (S)GGGGSGGGGSGGGGSGGGGS |
| 16 | (S)GGGGSGGGGSGGGGSGGGGSGGGGS |
| 17 | AAAGSG-GASAS |
| 18 | AAAGSG-XGGGS-GASAS |
| 19 | AAAGSG-XGGGSXGGGS-GASAS |
| 20 | AAAGSG-XGGGSXGGGSXGGGS-GASAS |
| 21 | AAAGSG-XGGGSXGGGSXGGGSXGGGS-GASAS |
| 22 | AAAGSG-XS-GASAS |
| 23 | PGGNRGTTTTRRPATTTGSSPGPTQSHY |
| 24 | ATTTGSSPGPT |
| 25 | ATTTGS |
| | GS |
| 26 | EPSGPISTINSPPSKESHKSP |
| 27 | GTVAAPSVFIFPPSD |
| 28 | GGGGIAPSMVGGGGS |
| 29 | GGGGKVEGAGGGGGS |
| 30 | GGGGSMKSHDGGGGS |
| 31 | GGGGNLITIVGGGGS |
| 32 | GGGGVVPSLPGGGGS |
| 33 | GGEKSIPGGGGS |
| 34 | RPLSYRPPFPFGFPSVRP |
| 35 | YPRSIYIRRRHPSPSLTT |
| 36 | TPSHLSHILPSFGLPTFN |
| 37 | RPVSPFTFPRLSNSWLPA |
| 38 | SPAAHFPRSIPRPGPIRT |
| 39 | APGPSAPSHRSLPSRAFG |
| 40 | PRNSIHFLHPLLVAPLGA |
| 41 | MPSLSGVLQVRYLSPPDL |
| 42 | SPQYPSPLTLTLPPHPSL |
| 43 | NPSLNPPSYLHRAPSRIS |
| 44 | LPWRTSLLPSLPLRRRP |
| 45 | PPLFAKGPVGLLSRSFPP |
| 46 | VPPAPVVSLRSAHARPPY |
| 47 | LRPTPPRVRSYTCCPTP- |

TABLE 2-continued

Flexible linker sequences

| SEQ ID NO: | SEQUENCE |
|---|---|
| 48 | PNVAHVLPLLTVPWDNLR |
| 49 | CNPLLPLCARSPAVRTFP |

(S) is optional in sequences 13 to 16.

Examples of rigid linkers include the peptide sequences GAPAPAAPAPA (SEQ ID NO:94), PPPP (SEQ ID NO:95) and PPP.

In one embodiment $X_1$ is selected:

| SEQ ID NO: | SEQUENCE |
|---|---|
| 50 | AKTTPKLEEGEFSEAR |
| 51 | AKTTPKLEEGEFSEARV |
| 52 | AKTTPKLGG |
| 53 | SAKTTPKLGG |
| 54 | AKTTPKLEEGEFSEARV |
| 55 | SAKTTP |
| 56 | SAKTTPKLGG |
| 57 | RADAAP |
| 58 | RADAAPTVS |
| 59 | RADAAAAGGPGS |
| 60 | RADAAAA(G$_4$S)$_4$ |
| 61 | SAKTTPKLEEGEFSEARV |
| 62 | ADAAP |
| 63 | ADAAPTVSIFPP |
| 64 | TVAAP |
| 65 | TVAAPSVFIFPP |
| 66 | QPKAAP |
| 67 | QPKAAPSVTLFPP |
| 68 | AKTTPP |
| 69 | AKTTPPSVTPLAP |
| 70 | AKTTAP |
| 71 | AKTTAPSVYPLAP |
| 72 | ASTKGP |
| 73 | ASTKGPSVFPLAP |
| 74 | GENKVEYAPALMALS |
| 75 | GPAKELPLKEAKVS |
| 76 | GHEAAAVMQVQYPAS |
| 77 | SAKTTP |
| 78 | TVSSASTKGP |
| 79 | EIKRTTVAAPS |
| 96 | EIKRTVAAPS |
| 97 | RTVAAP |

In one embodiment $X_1$ is a peptide linker which is an albumin binding peptide.

Examples of albumin binding peptides are provided in WO 2007/106120 and include:

TABLE 3

| SEQ ID NO: | SEQUENCE |
|---|---|
| 80 | DLCLRDWGCLW |
| 81 | DICLPRWGCLW |
| 82 | MEDICLPRWGCLWGD |
| 83 | QRLMEDICLPRWGCLWEDDE |
| 84 | QGLIGDICLPRWGCLWGRSV |
| 85 | QGLIGDICLPRWGCLWGRSVK |
| 86 | EDICLPRWGCLWEDD |
| 87 | RLMEDICLPRWGCLWEDD |
| 88 | MEDICLPRWGCLWEDD |
| 89 | MEDICLPRWGCLWED |
| 90 | RLMEDICLARWGCLWEDD |
| 91 | EVRSFCTRWPAEKSCKPLRG |
| 92 | RAPESFVCYWETICFERSEQ |
| 93 | EMCYFPGICWM |

$X_1$ in the heavy and light chain may be selected independently. However, in one embodiment $X_1$ in the heavy chain and light chain are identical.

It will be appreciated that one or more amino acid substitutions, additions and/or deletions may be made to the antibody variable domains, provided by the present invention, without significantly altering the ability of the antibody to bind to target antigen and to neutralise activity thereof. The effect of any amino acid substitutions, additions and/or deletions can be readily tested by one skilled in the art, for example by using the in vitro assays, for example a BIAcore assay.

The constant region domains and Fc regions of the binding protein of the present invention may be selected having regard to the proposed function of the antibody molecule, in particular the effector functions which may be required, and for example, may be human IgA, IgD, IgE, IgG or IgM domains. In particular, human IgG may be used, especially of the IgG1 and IgG3 isotypes when the binding protein is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

In one embodiment the disclosure provides a pair of binding proteins. A pair of binding proteins may be referred to herein as an antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule.

Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{77}$, Bismuth$^{213}$, Califomium$^{252}$, Iridiuml$^{92}$ and Tungsten188/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties, and the PEG molecules may be attached through any available amino acid side-chain or terminal amino acid functional group located in the antibody fragment, for example any free amino, imino, thiol, hydroxyl or carboxyl group. Such amino acids may occur naturally in the antibody or may be engineered into the fragment using recombinant DNA methods (see for example U.S. Pat. Nos. 5,219,996; 5,667,425; WO 98/25971). In one example the antibody molecule of the present invention comprises a modified C-terminal wherein the modification is the addition to the C-terminal end of its heavy chain one or more amino acids to allow the attachment of an effector molecule. Alternatively or additionally, amino acids in the hinge may be added or inserted to form a modified hinge region containing one or more cysteine residues to which the effector molecule may be attached. Multiple sites can be used to attach two or more PEG molecules.

In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody fragment. Each polymer molecule attached to the modified portion of the antibody may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

The present invention also provides isolated DNA encoding a binding protein described herein or a fragment thereof of a heavy or light chain thereof.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In a further aspect there is provided a host cell comprising said vector and/or DNA.

Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of a binding protein according to the present invention comprising culturing a host cell containing a vector (and/or DNA) of the present invention under conditions suitable for leading to expression of protein from DNA encoding the binding protein of the present invention, and isolating the binding protein.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide.

Alternatively, a single vector may be used, the vector including sequences encoding light chain and heavy chain polypeptides.

The binding protein and fragments according to the present disclosure are expressed at suitable levels from host cells. Thus the properties of the antibodies and/or fragments may be conducive to commercial processing.

The binding protein of the present invention is useful in the treatment and/or prophylaxis of a pathological condition.

Thus there is provided a binding protein for use in treatment, by administering a therapeutically effective amount thereof. In one embodiment the antibody or single chain component thereof is administered in a pharmaceutical formulation.

The present invention also provides a pharmaceutical or diagnostic composition comprising a binding protein of the present invention in combination with one or more of a pharmaceutically acceptable excipient, diluent or carrier. Accordingly, provided is the use of a binding protein of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the binding protein of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhitor is a small molecule. In another embodiment the inhibitor is an antibody specific to the target.

The pharmaceutical compositions suitably comprise a therapeutically effective amount of the binding protein of the invention. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which a binding protein of the present invention is administered depends on the nature of the condition to be treated, the extent of the inflammation present and on whether the antibody molecule is being used prophylactically or to treat an existing condition.

The frequency of dose will depend on the half-life of the binding protein and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the binding protein may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the binding protein or fragment, for example if the pH of the formulation is 7 then a pI of from 8-9 or above may be appropriate. Whilst not wishing to be bound by theory it is thought that this may ultimately provide a final formulation with improved stability, for example the binding protein or fragment thereof remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the binding protein from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the binding protein or fragment) is of primary importance.

The propellent gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension or solution may be prepared from, for example, a lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) in particular packed in foil envelopes. Each vial contains a unit dose in a volume, e.g., 2 mL, of solvent/solution buffer.

The binding protein of the present disclosure are thought to be suitable for delivery via nebulisation.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

DESCRIPTION OF THE DRAWINGS

FIG. 1 shows a diagrammatic represents of a DVD-Ig molecule.

FIG. 2 to 4 shows various representations of a light and heavy chain format according to the present disclosure.

FIG. 5: shows SDS-PAGE analysis of Protein-G purified anti-A/anti-C DVD-Ig+ds and anti-A/anti-C DVD-Ig.

FIG. 6: SDS-PAGE analysis of Protein-A purified anti-B/anti-C DVD-Ig+ds and anti-B/anti-C DVD-Ig

EXAMPLE 1

Generation and Analysis of a Disulphide Stabilized Anti-A/Anti-C DVD-Ig

Construction of Anti-A/Anti-C DVD-Ig+Ds (Anti-A Outer, Anti-C Inner) and Anti-A/Anti-C DVD-Ig (Anti-A Outer, Anti-C Inner) Plasmids The total light chain variable region consisting of anti-A variable—linker (RTVAAP (SEQ ID NO:97))—anti-C variable was purchased from DNA2.0 and cloned as a HindIII/BsiW1 fragment into a UCB mammalian expression human kappa light chain vector under the control of the HCMV-MIE promoter and SV40E polyA sequence. The total heavy chain variable region consisting of anti-A variable—linker (ASTKGP (SEQ ID NO:72))—anti-C variable was purchased from DNA2.0 and cloned as a HindIII/Xho1 fragment into a UCB mammalian expression human IgG1 heavy chain vector under the control of the HCMV-MIE promoter and SV40E polyA sequence. Disulphide stabilization of the outer (anti-A) variable region was achieved by mutation to cysteine at position 44 of the heavy chain and 100 of the light chain using the QuikChange Lightening Site directed mutagenesis kit from Agilent Technologies following the manufacturer's protocol. Two 30 base pair oligos were designed for introducing the cysteine mutation at the heavy 44 and light 100 amino acid positions. The disulphide stabilized constructs were verified by sequencing.

Mammalian Expression of Anti-A/Anti-C DVD-Ig and Anti-A/Anti-C DVD-Ig+Ds

HEK293 cells were transfected with the heavy and light chain plasmids using Invitrogen's 293fectin transfection reagent according to the manufacturer's instructions. Briefly, 24 μg heavy chain plasmid and 24 μg light chain plasmid were incubated with 120 μl 293fectin and 4080 μl Optimem media for 20 mins at RT. The mixture was then added to $60\times10^6$ HEK293 cells in 60 ml suspension and incubated for 7 days with shaking at 37° C. After 7 days the supernatant was collected by centrifugation at 1500×g to remove the cells and then 0.22 μm sterile filtered.

Protein-G Quantification of Anti-A/Anti-C DVD-Ig and Anti-A/Anti-C DVD-Ig+Ds

The level of expression in the mammalian supernatants was assessed by a Protein-G HPLC method. Multiple cycles of protein-G purification were conducted on known amounts of standard antibody and unknown amounts of samples. The area of the elution peak followed by absorbance at 280 nm was measured and a standard curve created of known antibody amount verses elution peak area. The standard curve was used to convert sample elution peak areas to amounts of antibody with adjustment for differing extinction coefficients. The protein-G purification consisted of samples applied at 1 ml/min to a 1 ml Gammabind Plus Sepharose (GE Healthcare) column equilibrated in 20 mM sodium phosphate, 40 mM NaCl pH7.4. The column was washed with 20 mM sodium phosphate, 40 mM NaCl pH7.4 and the bound material eluted with 50 mM glycine/HCl pH2.7. The level of expression of anti-A/anti-C DVD-Ig+ds and anti-A/anti-C DVD-Ig are shown in Table 4. The introduction of disulphide stabilization of the anti-A variable region (outer v-region) had a minimal affect on expression level.

TABLE 4

| Expression level of anti-A/anti-C DVD-Ig and anti-A/anti-C DVD-Ig +ds | |
| --- | --- |
| | Expression level (μg/ml) |
| anti-A/anti-C DVD-Ig | 7.2 |
| anti-A/anti-C DVD-Ig +ds | 10.1 |

Protein-G Purification of Anti-A/Anti-C DVD-Ig and Anti-A/Anti-C DVD-Ig+Ds

The ~50 ml of 0.22 m filtered supernatants were concentrated to ~2 ml using Amicon Ultra-15 concentrators with a 10 kDa molecular weight cut off membrane and centrifugation at 4000×g in a swing out rotor. 1.8 ml of concentrated supernatant was applied at 1 ml/min to a 1 ml Gammabind Plus Sepharose (GE Healthcare) column equilibrated in 20 mM phosphate, 150 mM NaCl pH7.4. The column was washed with 20 mM phosphate, 150 mM NaCl pH7.4 and the bound material eluted with 0.1M glycine/HCl pH2.7. The elution peak was collected and pH adjusted to ~pH7 with 2M Tris/HCl pH8.8. The pH adjusted elution was concentrated and diafiltered into 20 mM phosphate, 150 mM NaCl pH7.4 using Amicon Ultra-15 concentrators with a 10 kDa molecular weight cut off membrane and centrifugation at 4000×g in a swing out rotor.

Figure 5:
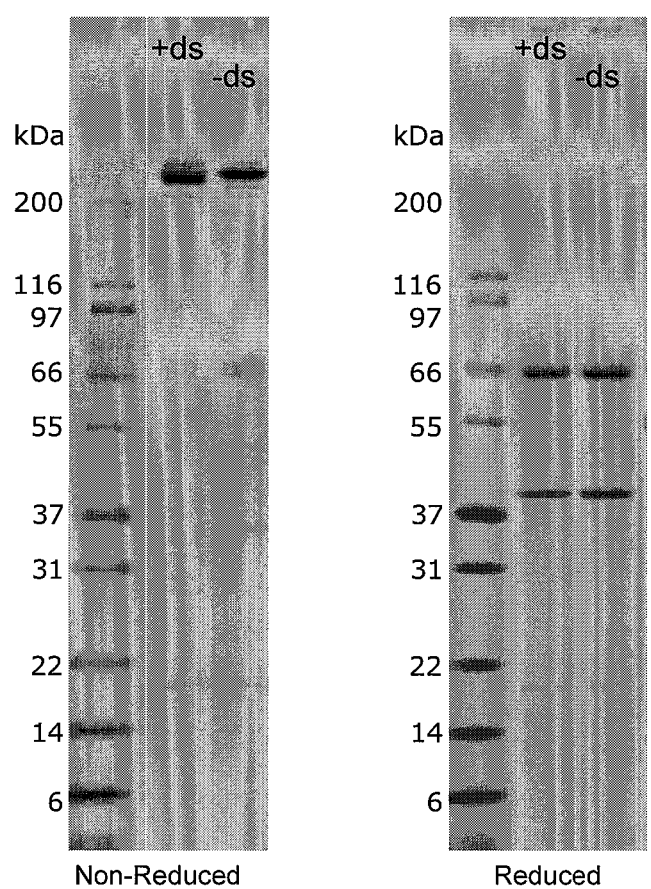
FIG. 5: shows SDS-PAGE analysis of Protein-G purified anti-A/anti-C DVD-Ig+ds and anti-A/anti-C DVD-Ig.

SDS-PAGE Analysis of Protein-G Purified Anti-A/Anti-C DVD-Ig and Anti-A/Anti-C DVD-Ig+Ds To 26 μl of Protein-G purified sample at ~0.1 mg/ml in PBS was added 10 μL 4×LDS (Invitrogen) sample running buffer. For non-reduced samples, 4 μL of 100 mM NEM was added and for reduced samples 4 μL of 10× reducing agent (Invitrogen) was added. The samples were vortexed, incubated at 100° C. for 3 mins, cooled and centrifuged at 12500 rpm for 30 secs. The prepared samples were loaded, 30 μl/~1.9 μg, on to a 4-20% acrylamine Tris/Glycine SDS gel and run for 110 mins at 125V. The gels were stained with Coomassie Blue protein stain and destained with 7.5% acetic acid, see FIG. 5. Under reducing conditions both anti-A/anti-C DVD-Ig and anti-A/anti-C DVD-Ig+ds run as 2 major bands at the same positions, one at ~65 kDa and one at ~40 kDa. The ~65 kDa band corresponds to the heavy chain and the ~40 kDa band to the light chain. There are also slightly more intense minor bands in anti-A/anti-C DVD-Ig compared to anti-A/anti-C DVD-Ig+ds suggesting that there is slightly more breakdown of the DVD-Ig when the stabilizing disulphide is absent. Under non-reducing conditions the main band for both anti-A/anti-C DVD-Ig and anti-A/anti-C DVD-Ig+ds is at ~250 kDa, however the main band for anti-A/anti-C DVD-Ig+ds is slightly lower than the main band for anti-A/anti-C DVD-Ig. This slightly smaller apparent size of the disulphide stabilized DVD-Ig is indicative of the formation of the stabilizing disulphide bond. Again there are also slightly more intense minor bands in anti-A/anti-C DVD-Ig compared to anti-A/anti-C DVD-Ig+ds suggesting that there is slightly more breakdown of the DVD-Ig when the stabilizing disulphide is absent.

Size Exclusion Analysis of Protein-G Purified Anti-A/Anti-C DVD-Ig and Anti-A/Anti-C DVD-Ig+Ds Protein-G purified samples were analysed by size exclusion HPLC. The samples were separated on a Superdex 200 10/300 GL Tricorn column (GE Healthcare) developed with an isocratic gradient of PBS pH7.4 at 1 ml/min. Peak detection was at 280 nm and apparent molecular weight was calculated by comparison to a standard curve of known molecular weight proteins verses elution volume. The introduction of disulphide stabilization of the anti-A variable region (outer v-region) had a minimal affect on the apparent size of the DVD-Ig (225 kDa (DVD-Ig) vs. 227 kDa (DVD-Ig +ds) but increased the percentage monomer by 10%. The increase in monomer was due to a decrease in both high molecular weight species and low molecular weight species.

Size Exclusion Purification of Protein-G Purified Anti-A/Anti-C DVD-Ig and Anti-A/Anti-C DVD-Ig+Ds 100 μl of the concentrated and diafiltered protein-G eluate was applied to a Superdex200 10/300GL Tricon column (GE Healthcare) equilibrated in 20 mM phosphate, 150 mM NaCl pH7.4. The column was developed with an isocratic gradient of 20 mM phosphate, 150 mM NaCl pH7.4 at 0.5 ml/min. 0.5 ml fractions were collected and the fraction which contained the apex of the monomer peak was retained for analysis.

BIAcore Affinity Analysis of Size Exclusion Purified Anti-A/Anti-C DVD-Ig and Anti-A/Anti-C DVD-Ig+Ds Binding affinities and kinetic parameters for the interaction of size exclusion purified monomer of anti-A/anti-C DVD-Ig and anti-A/anti-C DVD-Ig+ds with antigen C, A1 and A2 were determined by surface plasmon resonance (SPR) conducted on a Biacore T200 using CM5 sensor chips and HBS-EP (10 mM HEPES (pH7.4), 150 mM NaCl, 3 mM EDTA, 0.05% v/v surfactant P20) running buffer. The anti-A/anti-C DVD-Ig and anti-A/anti-C DVD-Ig+ds samples were captured to the sensor chip surface using an in-house generated anti-human CH1 monoclonal antibody. Covalent immobilisation of the capture antibody was achieved by standard amine coupling chemistry. Each assay cycle consisted of firstly capturing the anti-A/anti-C DVD-Ig or anti-A/anti-C DVD-Ig+ds using a 1 min injection, before an association phase consisting of a 3 min injection of antigen, after which dissociation was monitored for 20 min. After each cycle, the capture surface was regenerated with 2×1 min injections of 40 mM HCl followed by 30 s of 5 mM NaOH. The flow rates used were 10 μl/min for capture, 30 μl/min for association and dissociation phases, and 10 μl/min for regeneration. Titrations (1.1 nM to 30 nM) for each antigen, C, A1 and A2 were performed, a blank flow-cell was used for reference subtraction and buffer-blank injections were included to subtract instrument noise and drift. Kinetic parameters were determined by simultaneous global-fitting of the resulting sensorgrams to a standard 1:1 binding model using Biacore T200 Evaluation Software v1.0. The introduction of disulphide stabilization of the anti-A variable region (outer v-region) had a minimal affect on the affinities and stoichiometries of antigen binding for both the anti-A (outer) and anti-C (inner) variable regions against all antigens tested, see Table 5.

TABLE 5

| BIAcore affinity analysis of size exclusion purified anti-A/anti-C DVD-Ig and anti-A/anti-C DVD-Ig +ds | | | | | | |
| --- | --- | --- | --- | --- | --- | --- |
| | Antigen C | | Antigen A1 | | Antigen A2 | |
| | KD (pM) | Stoichio- metry | KD (pM) | Stoichio- metry | KD (pM) | Stoichio- metry |
| anti-A/anti-C DVD-Ig +ds | 813 | 0.54 | 4.10 | 1.06 | 15.2 | 1.10 |
| anti-A/anti-C DVD-Ig | 517 | 0.69 | 2.69 | 0.77 | 10.3 | 0.77 |

EXAMPLE 2

Generation and Analysis of Disulphide Stabilized Anti-B/Anti-C DVD-Ig

Construction of Anti-B/Anti-C DVD-Ig+Ds (Anti-B Outer, Anti-C Inner) and Anti-B/Anti-C DVD-Ig (Anti-B Outer, Anti-C Inner) Plasmids The total light chain variable region consisting of anti-B variable—linker (RTVAAP (SEQ ID NO:97))—anti-C variable was purchased from DNA2.0 and cloned as a HindIII/BsiW1 fragment into a UCB mammalian expression human kappa light chain vector under the control of the HCMV-MIE promoter and SV40E polyA sequence. The total heavy chain variable region consisting of anti-B variable—linker (ASTKGP (SEQ ID NO:72))—anti-C variable was purchased from DNA2.0 and cloned as a HindIII/XhoI fragment into a UCB mammalian expression human IgG1 heavy chain vector under the control of the HCMV-MIE promoter and SV40E polyA sequence. Disulphide stabilization of the outer (anti-B) variable region was achieved by mutation to cysteine at position 44 of the heavy chain and 100 of the light chain using the QuikChange Lightening Site directed mutagenesis kit from Agilent Technologies following the manufacturer's protocol. Two 30 base pair oligos were designed for introducing the cysteine mutation at the heavy 44 and light 100 amino acid positions. The disulphide stabilized constructs were verified by sequencing.

Mammalian Expression of Anti-B/Anti-C DVD-Ig and Anti-B/Anti-C DVD-Ig+Ds

HEK293 cells were transfected with the heavy and light chain plasmids using Invitrogen's 293fectin transfection reagent according to the manufacturer's instructions. Briefly, 24 µg heavy chain plasmid and 24 µg light chain plasmid were incubated with 120 µl 293fectin and 4080 µl Optimem media for 20 mins at RT. The mixture was then added to 60×10⁶ HEK293 cells in 60 ml suspension and incubated for 7 days with shaking at 37° C. After 7 days the supernatant was collected by centrifugation at 1500×g to remove the cells and then 0.22 µm sterile filtered.

Protein-G Quantification of Anti-B/Anti-C DVD-Ig and Anti-B/Anti-C DVD-Ig+Ds

The level of expression in the mammalian supernatants was assessed by a Protein-G HPLC method. Multiple cycles of protein-G purification were conducted on known amounts of standard antibody and unknown amounts of samples. The area of the elution peak followed by absorbance at 280 nm was measured and a standard curve created of known antibody amount verses elution peak area. The standard curve was used to convert sample elution peak areas to amounts of antibody with adjustment for differing extinction coefficients. The protein-G purification consisted of samples applied at 1 ml/min to a 1 ml Gammabind Plus Sepharose (GE Healthcare) column equilibrated in 20 mM sodium phosphate, 40 mM NaCl pH7.4. The column was washed with 20 mM sodium phosphate, 40 mM NaCl pH7.4 and the bound material eluted with 50 mM glycine/HCl pH2.7. The level of expression of anti-B/anti-C DVD-Ig+ds and anti-B/anti-C DVD-Ig are shown in Table 6. The introduction of disulphide stabilization of the anti-B variable region (outer v-region) had a minimal affect on expression level.

TABLE 6

| Expression level of anti-B/anti-C DVD-Ig and anti-B/anti-C DVD-Ig +ds | |
|---|---|
| | Expression level (µg/ml) |
| Anti-B/anti-C DVD-Ig | 5.9 |
| Anti-B/anti-C DVD-Ig +ds | 4.3 |

Protein-A Purification of Anti-B/Anti-C DVD-Ig and Anti-B/Anti-C DVD-Ig+Ds

The ~50 ml of 0.22 m filtered supernatants were concentrated to ~2 ml using Amicon Ultra-15 concentrators with a 30 kDa molecular weight cut off membrane and centrifugation at 4000×g in a swing out rotor. 1.8 ml of concentrated supernatant was applied at 1 ml/min to a 1 ml MabSelect SuRe (GE Healthcare) column equilibrated in 20 mM phosphate, 150 mM NaCl pH7.4. The column was washed with 20 mM phosphate, 150 mM NaCl pH7.4 and the bound material eluted with 0.1M sodium citrate pH3.4. The elution peak was collected and pH adjusted to ~pH7 with 2M Tris/HCl pH8.5. The pH adjusted elution was concentrated and diafiltered into 20 mM phosphate, 150 mM NaCl pH7.4 using Amicon Ultra-15 concentrators with a 10 kDa molecular weight cut off membrane and centrifugation at 4000×g in a swing out rotor.

Figure 6:
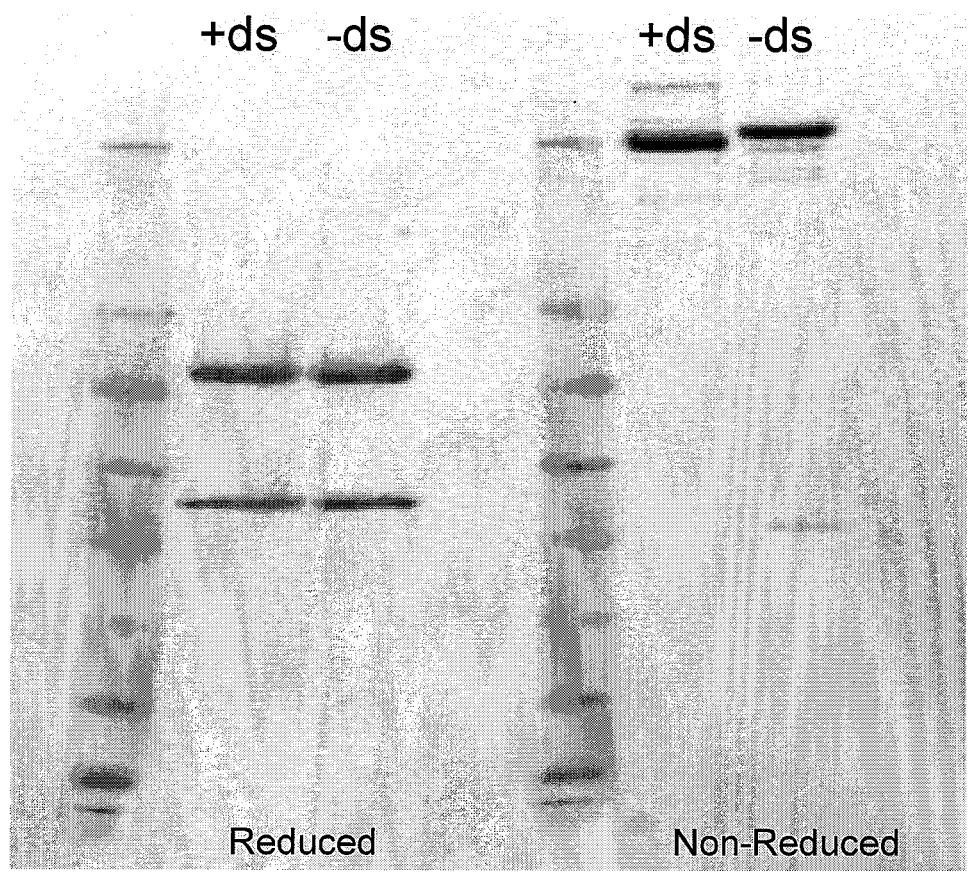
FIG. 6: SDS-PAGE analysis of Protein-A purified anti-B/anti-C DVD-Ig+ds and anti-B/anti-C DVD-Ig The variable domains are provided in each chain such that they form pre-defined pairs with suitable/adequate binding to a target antigen.

SDS-PAGE Analysis of Protein-A Purified Anti-B/Anti-C DVD-Ig and Anti-B/Anti-C DVD-Ig+Ds To 26 µl of Protein-A purified sample at ~0.1 mg/ml in PBS was added 10 µL 4×LDS (Invitrogen) sample running buffer. For non-reduced samples, 4 µL of 100 mM NEM was added and for reduced samples 4 µL of 10× reducing agent (Invitrogen) was added. The samples were vortexed, incubated at 100° C. for 3 mins, cooled and centrifuged at 12500 rpm for 30 secs. The prepared samples were loaded, 30 µl/~1.9 µg, on to a 4-20% acrylamine Tris/Glycine SDS gel and run for 110 mins at 125V. The gels were stained with Coomassie Blue protein stain and destained with 7.5% acetic acid, see FIG. 6. Under reducing conditions both anti-B/anti-C DVD-Ig and anti-B/anti-C DVD-Ig+ds run as 2 major bands at the same positions, one at ~65 kDa and one at ~40 kDa. The ~65 kDa band corresponds to the heavy chain and the ~40 kDa band to the light chain. Under non-reducing conditions the main band for both anti-B/anti-C DVD-Ig and anti-B/anti-C DVD-Ig+ds is at ~250 kDa, however the main band for anti-B/anti-C DVD-Ig+ds is slightly lower than the main band for anti-B/anti-C DVD-Ig. This slightly smaller apparent size of the disulphide stabilized DVD-Ig is indicative of the formation of the stabilizing disulphide bond.

Size Exclusion Analysis of Protein-A Purified Anti-B/Anti-C DVD-Ig and Anti-B/Anti-C DVD-Ig+Ds Protein-A purified samples were analysed by size exclusion HPLC. The samples were separated on a Superdex 200 10/300 GL Tricorn column (GE Healthcare) developed with an isocratic gradient of PBS pH7.4 at 1ml/min. Peak detection was at 280 nm. The introduction of disulphide stabilization of the anti-B variable region (outer v-region) increased the percentage monomer by 3%. The increase in monomer was due to a decrease in high molecular weight species.

Thermal Stability Analysis of Protein-A Purified Anti-B/Anti-C DVD-Ig and Anti-B/Anti-C DVD-Ig+Ds In quadruplicate, 9 µl of sample at 0.1 mg/ml in PBS was added to 1 µl of 30× stock of Sypro orange fluorescent dye in a 384 well plate. The plate was heated from 20-99° C.

using a 7900HT fast real-time PCR system and the fluorescence (excitation at 490 nm, emission at 530 nm) measured. Software is used to calculate the inflection point(s) of the unfolding curves, see Table 7. The introduction of disulphide stabilization of the anti-B variable region (outer v-region) has increased the thermal stability of this outer variable region by ~4° C.

TABLE 7

Thermal stability analysis of Protein-A purified anti-B/anti-C DVD-Ig and anti-B/anti-C DVD-Ig +ds.

|  | Tm (° C) | S.D. (° C.) |
|---|---|---|
| anti-B/anti-C DVD-Ig | 67.4 | 0.2 |
| anti-B/anti-C DVD-Ig +ds | 71.7 | 0.3 |

What is claimed is:

1. A binding protein, comprising:
a first polypeptide comprising:

$$VH_1\text{-}X_1\text{-}VH_2\text{-}CH\text{-}X_2$$

wherein $VH_1$ is a first heavy chain variable domain, $VH_2$ is a second heavy chain variable domain, CH is a constant domain, $X_1$ represents a flexible peptide linker that is one of SEQ ID NOs: 10 to 79, $X_2$ represents an Fc region, and
a second polypeptide comprising:

$$VL_1\text{-}X_1\text{-}VL_2\text{-}C$$

wherein $VL_1$ is a first light chain variable domain, $VL_2$ is a second light chain variable domain, C is a constant domain, and $X_1$ represents a flexible peptide linker that is one of SEQ ID NOs: 10 to 79,
wherein $VH_1$ and $VL_1$ form a first binding domain and $VH_2$ and $VL_2$ form a second binding domain; and
wherein there is a disulfide bond between $VH_1$ and $VL_1$.

2. The binding protein of claim 1, wherein the CH of the first polypeptide is linked to the C of the second polypeptide by a disulfide bond.

3. A pharmaceutically acceptable composition comprising the binding protein of claim 1.

4. The binding protein of claim 1 or a pharmaceutically acceptable composition comprising the binding protein of claim 1 for use in treatment.

5. The binding protein of claim 1, wherein the flexible peptide linker has a sequence corresponding to SEQ ID NO: 72.

6. The binding protein of claim 1, wherein the disulfide bond is between VH37 and VL95, VH44 and VL100, VH44 and VL105, VH45 and VL87, VH100 and VL50, VH98 and VL46, VH105 and VL43 and VH106 and VL57.

* * * * *